(12) United States Patent
Peter et al.

(10) Patent No.: US 7,786,443 B2
(45) Date of Patent: Aug. 31, 2010

(54) DUAL-MODALITY IMAGING

(75) Inventors: Jörg Peter, Schriesheim (DE); Ralf Schulz, München (DE)

(73) Assignee: Deutsches Krebsforschungszentrum Stiftung Des Oeffentlichen Rechts, Heidelberg (DE)

( * ) Notice: Subject to any disclaimer, the term of this patent is extended or adjusted under 35 U.S.C. 154(b) by 136 days.

(21) Appl. No.: 11/918,790

(22) PCT Filed: Apr. 10, 2006

(86) PCT No.: PCT/EP2006/061474
§ 371 (c)(1),
(2), (4) Date: Feb. 15, 2008

(87) PCT Pub. No.: WO2006/111485
PCT Pub. Date: Oct. 26, 2006

(65) Prior Publication Data
US 2009/0039268 A1 Feb. 12, 2009

(30) Foreign Application Priority Data
Apr. 19, 2005 (EP) .................................. 05008552

(51) Int. Cl.
*G01T 1/166* (2006.01)
(52) U.S. Cl. ................................. 250/363.04
(58) Field of Classification Search ............. 250/363.04
See application file for complete search history.

(56) References Cited

U.S. PATENT DOCUMENTS

| 3,927,318 A | * | 12/1975 | Macovski | 378/6 |
| 5,656,807 A | * | 8/1997 | Packard | 250/214 VT |
| 5,825,031 A | | 10/1998 | Wong et al. | |
| 2002/0049386 A1 | * | 4/2002 | Yang et al. | 600/476 |
| 2003/0195417 A1 | | 10/2003 | Wake et al. | |
| 2004/0021082 A1 | * | 2/2004 | Wong et al. | 250/367 |
| 2004/0081621 A1 | * | 4/2004 | Arndt et al. | 424/9.6 |
| 2004/0249260 A1 | * | 12/2004 | Wang et al. | 600/407 |

OTHER PUBLICATIONS

Weissleder et al., Nature Reviews Cancer, vol. 2, pp. 1-8, Jan. 2002.
Chatziioannou et al., European Journal of Nuclear Medicine, vol. 29, No. 1, pp. 98-114, Jan. 2002.
Ray et al., Cancer Research, vol. 63, pp. 1160-1165, Mar. 15, 2003.
Ronald G. Blasberg., Nuclear Medicine and Biology vol. 30, pp. 879-888, 2003.
Prout et al., "Detector concept for OPET, a combined PET and optical imaging system," 2003 IEEE Nuclear Science Symposium Conference Record/2003 IEEE Nuclear Science Symposium and Medical Imaging Conference, IEEE, vol. 5, 2003, pp. 2252-2256, XP010737502, ISBN: 0-7803-8257-9.

(Continued)

*Primary Examiner*—David P Porta
*Assistant Examiner*—Marcus H Taningco
(74) *Attorney, Agent, or Firm*—Birch, Stewart, Kolasch & Birch, LLP

(57) ABSTRACT

The invention relates to a dual-modality imaging system and a method for dual-modality imaging, wherein a positron emission tomography (PET) scanner for acquiring PET imaging data and at least one optical imaging detector for acquiring optical imaging data are arranged to acquire the PET imaging data and the optical imaging data of an imaged object (5) simultaneously (i.e. at the same time and at superimposed fields-of-view). The at least one optical imaging detector is a non-contact optical imaging detector.

25 Claims, 12 Drawing Sheets

OTHER PUBLICATIONS

Rannou et al., "Fully 3D System Model Estimation of OPET by Monte Carlo Simulation," Nuclear Science Symposium Conference Record, IEEE, 2004, pp. 3433-3436, XP010818678, ISBN: 0-7803-8700-7.

Rannou et al., "Investigation of OPET performance using GATE, a Geant4-based simulation softward," 2003 IEEE Nuclear Science Symposium Conference Records/2003 IEEE Nuclear Science Symposium and Medical Imaging Conference, IEEE, 2003, vol. 5, pp. 2048-2052, XP010736016, ISBN: 0-7803-8257-9.

* cited by examiner

DUAL-MODALITY IMAGING

FIELD OF THE INVENTION

The present invention relates to a dual-modality imaging system and a method for dual-modality imaging using a positron emission tomography (PET) scanner for acquiring PET imaging data and at least one optical imaging detector for acquiring optical imaging data.

BACKGROUND OF THE INVENTION

The qualitative and quantitative acquisition of morphological, functional and biochemical parameters using imaging methods is the basis for a plurality of medical research and application areas. An overview over known imaging methods is given in "Scaling down imaging: Molecular mapping of cancer in mice", R. Weissleder, Nat Rev Cancer (1/2002), Volume 2, 1-8. Two known imaging methods, which are applied e. g. in tumor research, are positron emission tomography (PET) and optical imaging techniques.

PET is a radiotracer imaging technique in which positron-emitting nucleids are administered into the imaged object. The positrons annihilate with surrounding electrons in the imaged object to produce a pair of gamma-rays, each having 511 keV of photon energy, travelling in nearly opposite directions. These gamma-rays are detected by a PET scanner which allows the determination of the location and direction in space of the trajectories of the gamma-rays. Tomographic reconstruction methods are then used to reconstruct a PET image from numerous determined trajectory lines. PET is a clinical imaging modality for non-invasive assays of biochemical processes. The imaging procedure can be repeatedly performed, thereby allowing each patient/animal to be used as its own control. Positron-labelled compounds have been synthesized for a variety of molecular targets, with examples of biological processes ranging from receptors and synthesis of transmitters in cell communication, to metabolic processes and gene expression. Subsequent transversal views of reconstructed projection or sinogram data of the imaged object developed by this technique are used to evaluate a variety of diseases. Clinical key objectives of PET in oncology are to determine and grade tumor mass, to establish whether a tumor is benign or malignant, to locate the site of primary disease, to detect metastatic disease, to identify multi-focal lesions, to determine the extent of tumors for treatment planning, to direct biopsy, to verify prognosis, to monitor response to treatment, to detect local or distant recurrence and to assess residual mass. In animal research, PET has been used extensively in the past for studies of non-human primates and other animals. Different PET-scanner designs for the imaging of small animals are described in "Molecular imaging of small animals with dedicated PET tomographs", A. F. Chatziioamiou, Eur J Nucl Med (2002) 29: 98-114.

Further imaging methods for in-vivo examination known in the state-of-the-art are optical imaging techniques including fluorescence or bioluminescence imaging. In fluorescence imaging, light of one excitation wavelength illuminates the imaged object, resulting in a shifted emission wavelength, that can be collected by CCD-cameras. The imaged object is labelled for this purpose using a variety of fluorescence probes. Smart probes have been developed, that can be activated and detected only when they interact with a certain target, e. g. a small molecule, peptide, enzyme substrate or antibody. Bioluminescence imaging is used to optically detect photons, that are emitted from cells, that have been genetically engineered to express luciferases, catalysts in a light generating reaction, through the oxidation of an enzyme-specific substrate (luciferin). Unlike fluorescence approaches, the imaged object does not need to be exposed to the light of an external light source, the technique being based upon the internal light produced by the luciferases.

Optical planar imaging and optical tomography (OT) are emerging as alternative molecular imaging modalities, that detect light propagated through tissue at single or multiple projections. A number of optical-based imaging techniques are available, from macroscopic fluorescence reflectance imaging to fluorescence imaging/tomography, that has recently demonstrated to localize and quantify fluorescent probes in deep tissues at high sensitivities at millimeter resolutions. In the near future, optical tomography techniques are expected to improve considerably in spatial resolution by employing higher-density measurements and advanced photon technologies, e. g. based upon modulated intensity light or very short photon pulses. Clinical optical imaging applications will require high efficient photon collection systems. While PET is a standard method in cancer diagnostics in humans for almost a decade now, OT has recently also found applications, such as imaging of breast cancer, brain function and gene expression in vivo. Primary interest for using optical imaging techniques lies in the non-invasive and non-hazardous nature of optical photons used, and most significantly in the availability of activateable probes that produce a signal only when they interact with their targets—as compared to radiolabelled probes which produce a signal continuously, independent of interacting with their targets, through the decay of the radioisotope. In OT, images are influenced greatly by the spatially dependent absorption and scattering properties of tissue. Boundery measurements from one or several sources and detectors are used to recover the unknown parameters from a transport model described, for instance, by a partial differential equation. The contrast between the properties of diseased and healthy tissue can be used in clinical diagnosis.

In the state of the art PET imaging and optical imaging are two imaging techniques, which are applied separately, using two separate devices successively. A single reporter gene, which is dual-labelled for PET and optical imaging, is described in "Optical bioluminouscence and positron emission tomography imaging of a novel fusion reporter gene in tumor xenografts of living mice" P. Ray et al., Cancer Research 63, 1160-1165, Mar. 15, 2003. Therein, a single substrate is dual-labelled and thus can be imaged by the two different imaging modalities. The imaged mice were therefor first scanned using a cooled CCD camera (optical imaging) followed by a separate micro PET scan.

Another paper describing a combination of the two techniques is "In-vivo molecular-genetic imaging: multi-modality nuclear and optical combinations", R. G. Blasberg, Nuclear Medicine and Biology 30 (2003) 879-888. By using multi-modality reporter constructs (coupled nuclear and optical reporter genes), which incorporate the opportunity for simultaneous PET, fluorescence and/or bioluminescence imaging, many of the shortcomings of each modality alone can be overcome. Until the presence, two separate imaging systems are used successively to acquire the imaging data of an imaged object with such multi-modality reporters.

A comparison of the images obtained by the two imaging methods is possible only to a limited extent since they cannot be obtained simultaneously. The problems of excessive and prolonged burdening of the subject to be examined, the non-reproducibility of kinetic studies, the non-identical imaging geometries, animal and organ movement and the correct superposition of the images arise, when the two methods are carried out successively.

In D. Prout et. al: <<Detector Concept for OPET, a Combined PET and Optical Imaging System>>, 2003 IEEE Nuclear Science Symposium Conference Record, vol. 5 (2003-10-19), pages 2252-2256, ISBN: 0-7803-8257-9 an imaging system is presented, which is described as being capable of detecting and simultaneously imaging both PET and optical signals generated by bioluminescence probes, only. In this imaging system modified PET detectors are used for both, γ-ray detection and optical imaging. As a precondition for the optical imaging the surface of the imaged object needs to be in contact with the crystals of the PET detector in order to define a field-of-view for optical photons. This condition, however, cannot be achieved for complex geometrical objects such as mice, so that the proposed device produces optical projections of low quality. The presented imaging system is not capable of fluorescence imaging and is classified as a measurement device, which has to be in contact with the measured object. The device described by Prout et. al. used for optical imaging does not incorporate a laser or other light source. This is the reason why this device has only been used for bioluminescence imaging, not however for fluorescence imaging which requires an external light source. Furthermore a PET detector is not designed as an optical imaging detector and is not sufficiently sensitive to light photons.

SUMMARY OF THE INVENTION

Therefore, the present invention is based on the object of avoiding the disadvantages of the prior art and of combining the advantages of the two technologies described above.

This object is achieved by means of a dual-modality imaging system, wherein a positron emission tomography (PET) scanner for acquiring PET imaging data and at least one optical imaging detector for acquiring optical imaging data are arranged to acquire the PET imaging data and the optical imaging data of an imaged object simultaneously (i.e. at the same time and at superimposed fields-of-view), the at least one optical imaging detector being a non-contact optical imaging detector.

The most innovative aspect of the proposed system is that it is possible to perform unified simultaneous acquisition, reconstruction and tracers/probe-kinetic modeling e.g. for dual-modality small animal imaging. The dual-modality imaging can provide the potential for understanding of integrative biology, earlier detection and characterization of disease, and evaluation of treatment. The use of this novel imaging system will drive towards a new standard that allows linking established in-vitro and cell culture experimental assays to imaging studies within living subjects across the particular imaging modalities.

Since both regional distribution and time variation of the underlying multi-variate photon distributions are acquisition and subject specific and diversify by variations thereof, and imaging procedures cannot be performed repeatedly at short time intervals of the same living object in many cases, combined and simultaneous imaging is possible with this novel system carrying clearly advantageous potential. Further advantages are simultaneous recording of tracer kinetics, less subject encumbrance, and identical imaging geometries. The proposed nuclear-optical tomographic imaging systems have the potential to accurately quantify fluorescence and bioluminescence in deep heterogeneous media in-vivo. The invention supports the development of generalized reporter probes where the underlying labelling chemistry (radio isotope, optical marker) remains relatively similar but the underlying molecular structure can be easily modified to image a new molecular target. The system enables imaging assays that are more sensitive to low-level biological events. Furthermore, the imaging system should be generally less cost-expensive than its submodality counterparts and can be housed in shared resources of basic science laboratories.

The dual-modality imaging system and method according to the present invention have the potential to foster interdisciplinary research, that will lead to the development of new reporter constructs, to a better understanding of mechanisms of disease and response to therapy, the processes involved e. g. leading to an understanding of tumor initiation, growth, angiogenesis, metastasis, immune response.

The present invention makes non-invasive fully tomographic simultaneous non-contact image acquisition of dual-labelled (near-infrared) fluorescent, bioluminescent and positron emitting molecular markers possible in small objects at identical fields-of-view, particularly in mice and rats, but also in specific human organs and tissues such as breast and skin. The invention solves problems connected to separately imaging targets with different devices, as for instance the direct study of tracer/marker kinetics, image registration, time-resolved concurrent data analysis and animal handling which are inaccessible (kinetics) or become crucial (registration, animal management). The invention assesses visual representation, characterization, and quantification of biological processes at the cellular and sub-cellular levels within intact living organisms by means of simultaneously performing image acquisition procedures. The invention proposes imaging systems, which are highly sensitive in identifying location, magnitude and time variation of specific molecular events (e. g. gene expression and enzyme activity) by simultaneously detecting different tracer and marker types in vivo.

Another advantage of the dual-modality imaging system according to the present invention is that the at least one optical imaging detector is designed as a non-contact detector. According to the present invention, the detector is not in contact with the imaged object, unlike known fibre-optics based optical imaging design with fibre ending tips being placed in contact with the object. The non-contact optical detector of the present invention has significant advantages in view of simplifying the handling of the imaged object (e.g. a living animal), reducing the experimental complexity and simplifying the study management.

In the preferred embodiment of the present invention, the at least one optical imaging detector and the PET scanner are mounted on a rotatable common gantry. The gantry guarantees a fixed relationship between the optical imaging detector (s) and the PET scanner during imaging data acquisition, even when the devices are moved in relation to the imaged object. Preferably, the gantry (and with it the scanner and detectors) is rotatable (e. g. around a longitudinal axis of the imaged object) and translatable (e. g. along the longitudinal axis of the imaged object). The gantry with the optical imaging detector and the PET scanner can be rotatable around its vertical and/or its longitudinal axis. The gantry can be rotatable for 360° to allow an arbitrary radial positioning of the optical imaging detector and to allow tomographic imaging.

The PET scanner of the dual-modality imaging system according to the present invention preferably comprises at least two gamma-ray detector arrays. Gamma-ray detector arrays are known in prior art, usually including arrays of scintillation crystals and a plurality of photodetectors e. g. position-sensitive photomultiplier tubes. The gamma-ray detector arrays and the at least one optical imaging detector are preferably radially relocatable. The radial relocation is in this context referring to the position of the imaged object, which means that the distance between the gamma-ray detector arrays or the optical imaging detector and the imaged object can be varied. Therefore, the position of the gamma-ray detector arrays and of the optical imaging detector(s) can be adapted to different imaged objects of different forms and sizes before acquiring imaging data.

According to one embodiment of the present invention, the PET scanner comprises two opposed planar gamma-ray detector arrays. The two opposed detector arrays are provided to detect two gamma-rays emitted within the imaged object, which are travelling in opposite directions. The at least one optical imaging detector is preferably arranged adjacent to the planar gamma-ray detector arrays in a plane which is perpendicular to the planar gamma-ray detector arrays. This dual-modality imaging system can comprise for example two opposed optical imaging detectors, e. g. two opposed CCD cameras.

CCDs (charge coupled devices) are charge coupled imaging sensors that serve for highly sensitive detection of photons. The CCD camera is divided into a multiplicity of small light-sensitive zones (pixels) which produce the individual points of an image. The grid of the pixels is formed by a circuit structure on a semiconductor crystal (usually silicon). The method of operation of the CCD camera is based on the liberation of electrons by impinging light in the semiconductor material. A photon falling onto a pixel liberates at least one electron that is held fixed by an electrical potential at the location of the pixel. The number of electrons liberated at the location of the pixel is proportional to the intensity of the light incident at that location. The number of electrons is measured in each pixel, with the result that an image can be reconstructed. CCDs should be cooled since otherwise more electrons would be read out which would not be liberated as a result of the light incidence but rather as a result of heating. In the case of the present invention, the optical photons of the bioluminescent and/or fluorescent markers are according to one preferred embodiment of the present invention detected with the aid of at least one CCD camera.

Using two opposed planar gamma-ray detector arrays and two adjacent optical imaging detectors (e. g. CCD cameras) has the advantage that the planar detector arrays and the optical imaging detectors can be adjusted in their separation (being radially relocatable) in order to optimize detection efficiency with different-sized imaged objects (e. g. laboratory animals). In order to acquire tomographic data, the gantry holding the two gamma-ray detector arrays and the two optical imaging detectors rotates at 180 degrees single-step mode around the imaged object during data acquisition.

In another preferred embodiment of the present invention the PET scanner comprises a plurality of planar or curved gamma-ray detector arrays, which are arranged in a cylindrical ring form. The ring of detector arrays surrounds the imaged object during imaging data acquisition. Preferably, in this ring form arrangement, two of the gamma-ray detector arrays at a time are diametrically opposed, wherein two opposed detector arrays are provided to detect two gamma-rays emitted within the imaged object, which are travelling in opposite directions. The radius of the ring form can be varied, the gamma-ray detectors being radially relocatable, in order to adapt the system to different imaged objects.

One possible embodiment of the dual-modality imaging system with gamma-ray detectors arranged in a ring form, comprises at least one optical imaging detector (e. g. CCD camera), which is integrated into the ring form. This can be achieved by replacing one or more gamma-ray detector blocks of the PET scanner in the ring by one or more optical imaging detectors (e. g. CCD cameras). For this purpose, the lenses of CCD cameras can be purposely manufactured or selected to fit within the given block geometry of the PET scanner. The built-in CCD cameras will have the same image characteristics and performance standards as compared to separate dedicated application. The CCD chips might also be cooled in order to lower quantum noise. Replacing PET gamma-ray detector arrays (blocks) essentially corresponds to a truncated data acquisition problem, which can be compensated for within the imagery construction algorithm of the PET data.

In another possible embodiment of the dual-modality imaging system with gamma-ray detectors arranged in a ring form, the ring form is tilted about a first angle in one direction and the at least one optical imaging detector is tilted about a second angle in an opposite direction with respect to the imaged object. Preferably, the first angle is in the range from 5 to 25° and the second angle is in the range from 5 to 25°. The two angles, however, can be chosen in a range from 0° to 90°. The degree of tilting is adjustable, depending on the camera parameters, the imaged object size and imaging task. Images acquired (and reconstructed) for both modalities (PET and optical) can be corrected for the tilting angle inversely by simple numeric algebra. Preferably, the dual-modality imaging system comprises a ring of gamma-ray detector arrays which is tilted in one direction (e. g. relative to the vertical axis of the imaged object) and one CCD camera, which is tilted in the other direction (e. g. relative to the vertical axis of the imaged object).

The optical imaging detector of the dual-modality imaging system according to the present invention preferably comprises at least one photo detector.

A photo detector is a sensor, which is arranged to detect photons emitted from the imaged object. The photo detector comprises for example at least one CCD camera or at least one photo diode. Preferably the at least photo detector is a position sensitive photo detector, which detects photons and the position of their entering the photo detector. Examples for position sensitive photo detectors are a CCD (charge-coupled device) based detector, an APD (avalanche photo diode) array, a photo diode array or a CMOS (complementary metal-oxide semiconductor) sensor. An APD array or a photo diode array contains a plurality of APDs or photo diodes respectively, which is arranged in an array.

In another preferred embodiment of the present invention, the optical imaging detector comprises at least one micro-lens array with a plurality of micro-lenses.

In one preferred embodiment of the present invention, each micro-lens is connected to an optical fibre. The advantage of this embodiment is that each fibre-coupled photo detector element has its own individual dynamics. Preferably each micro-lens is connected to a photo detector (e.g. a photo diode) or to a light source via an optical fibre. These optical fibres can take on two different purposes: either the light collected by the micro-lenses will be tracked through the fibres to the photo detectors for detection or light from the light source (e.g. laser diode) is tracked through the fibres to the imaged object, e.g. for fluorochrome excitation.

In another preferred embodiment of the present invention, at least one position sensitive photo detector, preferably a large field CMOS sensor, is positioned at a focal plane of one of the micro-lens arrays. In this case, no optical fibres are needed to transfer photons from the micro-lenses of the micro-lens array to the photo detector, thus simplifying the detector construction.

One immediate advantage of detectors with micro-lens arrays, as compared to CCD cameras, lies in the locally adaptive dynamic range of the optical system. As a consequence, the dynamic range of the over-all tomographical optical system is greatly improved, allowing for fast (parallel) fully tomographic projection data acquisition, independent of laser excitation position and pattern. Each micro-lens has preferably a diameter in the range from 0.1 to 2 mm. By way of example with a lens diameter of 1 mm and an overall array size of 1 cm times 1 cm one micro array assembles 100 lenses allowing for 1 mm spatially separated lens pitch—which subsequently corresponds to the intrinsic spatial detection resolution of the optical system.

The micro-lens array can for example have a square, rectangular or hexagonal pattern. An optical collimator can be positioned in front of each micro-lens array. Such an optical collimator is preferably a multi-hole collimator which is adapted to the micro-lens array. The dual-modality imaging system according to the present invention comprises in a preferred embodiment a plurality of planar or curved micro-lens arrays, which are arranged in a ring structure. Alternatively to optical fibre coupled micro-lens arrays a plurality of optical detectors comprising position sensitive photo detectors can be arranged in a ring structure. These ring structures can be arranged within a ring form of gamma-ray detector arrays.

The optical imaging detector comprising micro-lens arrays arranged in a ring structure has the advantage (for example over a CCD-based system) of allowing the complete and three-dimensional tomographic optical imaging of an object with an improved dynamic range (sensitivity).

The present invention therefore also refers to a method for dual-modality imaging of an imaged object wherein PET imaging is combined with a non-contact three-dimensional optical imaging method, wherein the optical imaging data of the imaged object is acquired by an optical imaging detector comprising micro-lens arrays arranged in a ring structure with the purpose of collimating optical photons emitted from the imaged object to form light projection data for further detection, the micro-lens array ring structure surrounding the imaged object.

The present invention furthermore relates to a method for dual-modality imaging of an imaged object wherein PET imaging data and optical imaging data of the imaged object are acquired simultaneously by a PET scanner and at least one optical imaging detector. The design and function of the PET scanner and the optical imaging detector(s) used for this method are similar to the ones described above. This method preferably includes the steps of reconstructing a PET image and an optical image by the acquired PET and optical imaging data and displaying at least one of the PET image, the optical image or a fused PET/optical image on a display device.

The present invention can be applied in medical imaging in general. Arrays of major applications can be positioned in molecular biology, genetic research, oncology, cancer research, pharmacology and drug research. Primary tasks and intended applications for the imaging system according to the present invention are as follows: to image specific cellular and molecular processes, e. g. gene expression, or more complex molecular interactions such as protein-protein interactions, to monitor multiple molecular events simultaneously, to track single or dual-labelled cells, to optimize drug and gene therapy, to image drug effects at molecular and cellular level, to assess disease progression at a molecular pathological level, to create the possibility of achieving all of the above goals of imaging in a single, rapid, reproducible and quantitative manner. For further applications specific use of the present invention is to monitor time-dependent experimental, developmental, environmental and therapeutic influences on gene products in the same animal (or patient), to study the interaction of tumor cells and the immune system, to study viral infections by marking the virus of interest with a reporter gene, and others. There is also an enormous clinical potential for the non-invasive assessment of endogeneous and exogeneous gene expression in vivo (gene (DNA), message (RNA), protein, function), for imaging receptors, enzymes, transporters, for novel applications in basic and translational research (gene therapy), for early detection of disease, for guidance of therapeutic choices, for monitoring drug action, for aid of pre-clinical drug development, for non-invasive and repetitive monitoring of gene therapy and for optimizing clinical trials of human gene therapy.

The present invention is explained in greater detail below with reference to the drawing.

DESCRIPTION OF THE FIGURES

FIG. 1 shows a first preferred embodiment of a dual-modality imaging system according to the present invention.

In the case of this preferred embodiment of the present invention, the dual-modality imaging system according to the invention comprises two CCD cameras 1, 2 facing one another and a PET scanner with two opposed planar gamma-ray detector arrays 3, 4, which are arranged adjacent to the CCD cameras 1, 2. The CCD cameras 1, 2 are arranged in a plane, which is perpendicular to the planar gamma-ray detector arrays 3, 4. An imaged object 5 is surrounded by the CCD cameras 1, 2 and the detector arrays 3, 4. By way of example, the shown dual-modality imaging system is a Dual-Head PET-OT system with a YSO/LSO phoswitch PET detector with 1.8×1.8×6/12 mm crystals resulting in a 74 mm² field-of-view.

Figure 2:
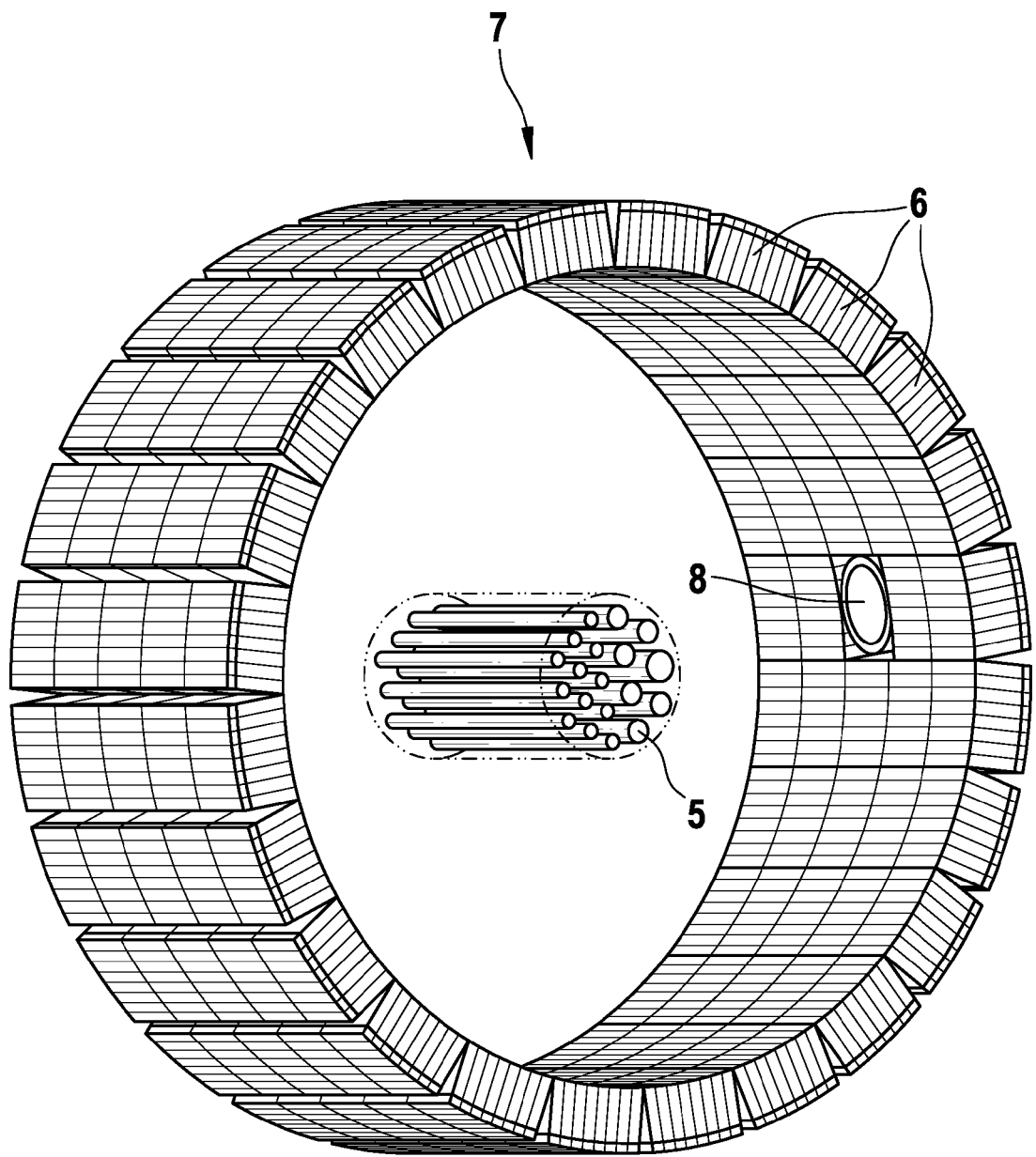
FIG. 2 shows schematically a second preferred embodiment of a dual-modality imaging system according to the invention with a CCD camera, which is integrated into a ring of rotatable gamma-ray detector arrays.

FIG. 2 shows a second preferred embodiment of a dual-modality imaging system according to the present invention.

This dual-modality imaging system comprises a plurality of gamma-ray detector arrays 6, which are arranged in a ring form 7 surrounding the imaged object 5. Into this ring form 7 a CCD camera 8 is integrated, replacing one of the gamma-ray detector arrays 6. By way of example, the cylindrical PET scanner can be an LSO detector (2.1×2.1×10 mm) with a 78 mm axial field of view (FOV) and 148 mm ring diameter.

Figure 3:
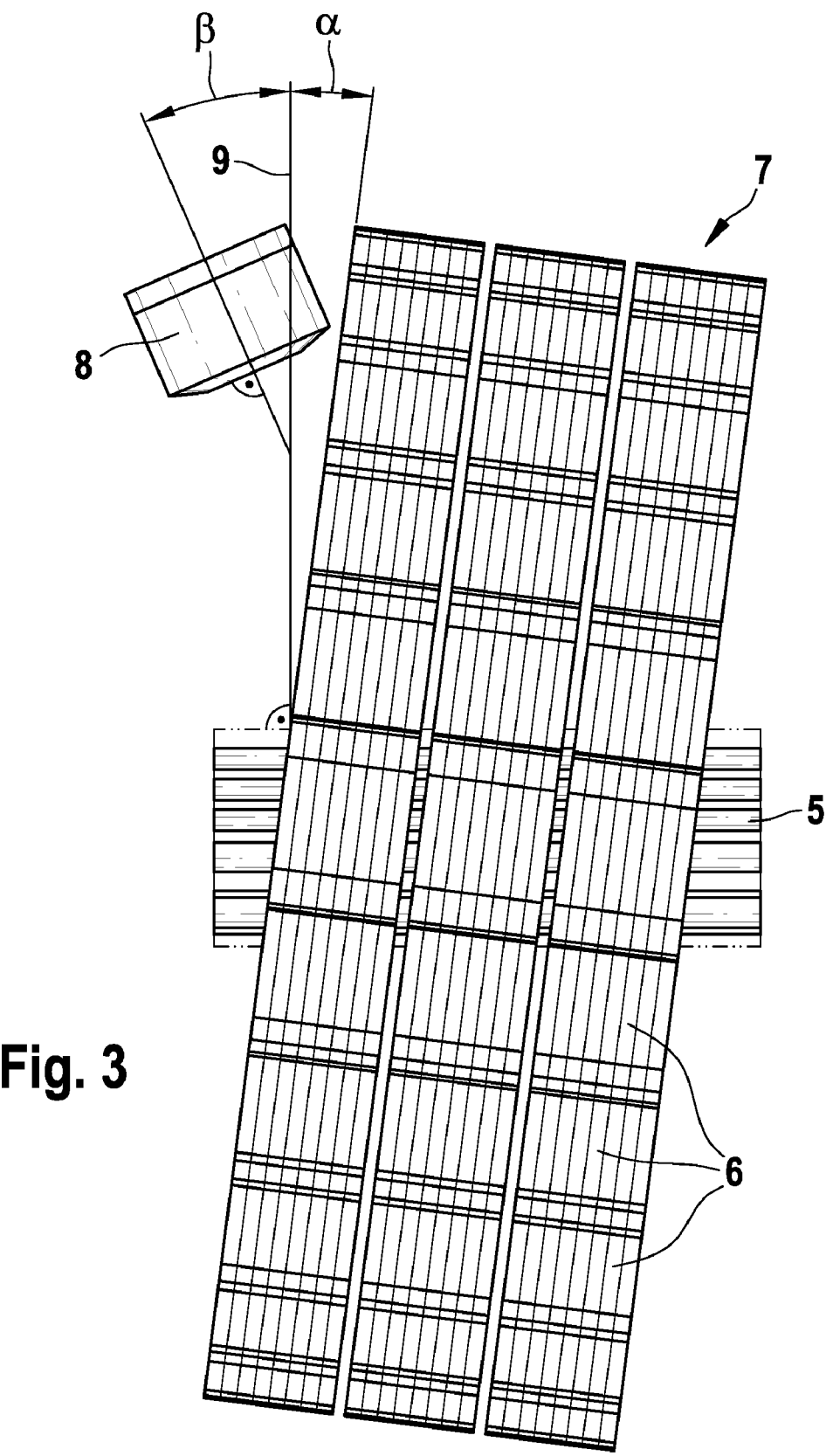
FIG. 3 shows schematically a third preferred embodiment of a dual-modality imaging system according to the invention with a tilted ring of gamma-ray detector arrays and a tilted CCD camera.

FIG. 3 shows a third preferred embodiment of a dual-modality imaging system according to the present invention.

In this case, the PET scanner comprises a plurality of gamma-ray detector arrays 6, which are arranged in a ring form 7, surrounding the imaged object 5. The ring form 7 is tilted about a first angle $\alpha$ in one direction and the CCD camera 8, which is serving as an optical imaging detector, is tilted about a second angle $\beta$ in an opposite direction with respect to (the vertical axis 9 of) the imaged object 5. The PET scanner ring 7 is in this case rotated by $\alpha=8$ degrees in one direction and the CCD camera 8 by $\beta=18$ degrees in the other direction. In this example, the tilting angle $\alpha$ of the PET ring 7 is smaller, because its spatial resolution is non-isotropic, i.e. it is higher axially than it is transaxially, and because its field-of-view is axially limited, depending on the number of detector rings. By way of example, this dual-modality imaging system can be a tilted PET-OT LYSO/LuYAP detector (2×2×9) with a 54 mm axial field of view (FOV) and 114 mm ring diameter.

Figure 1:
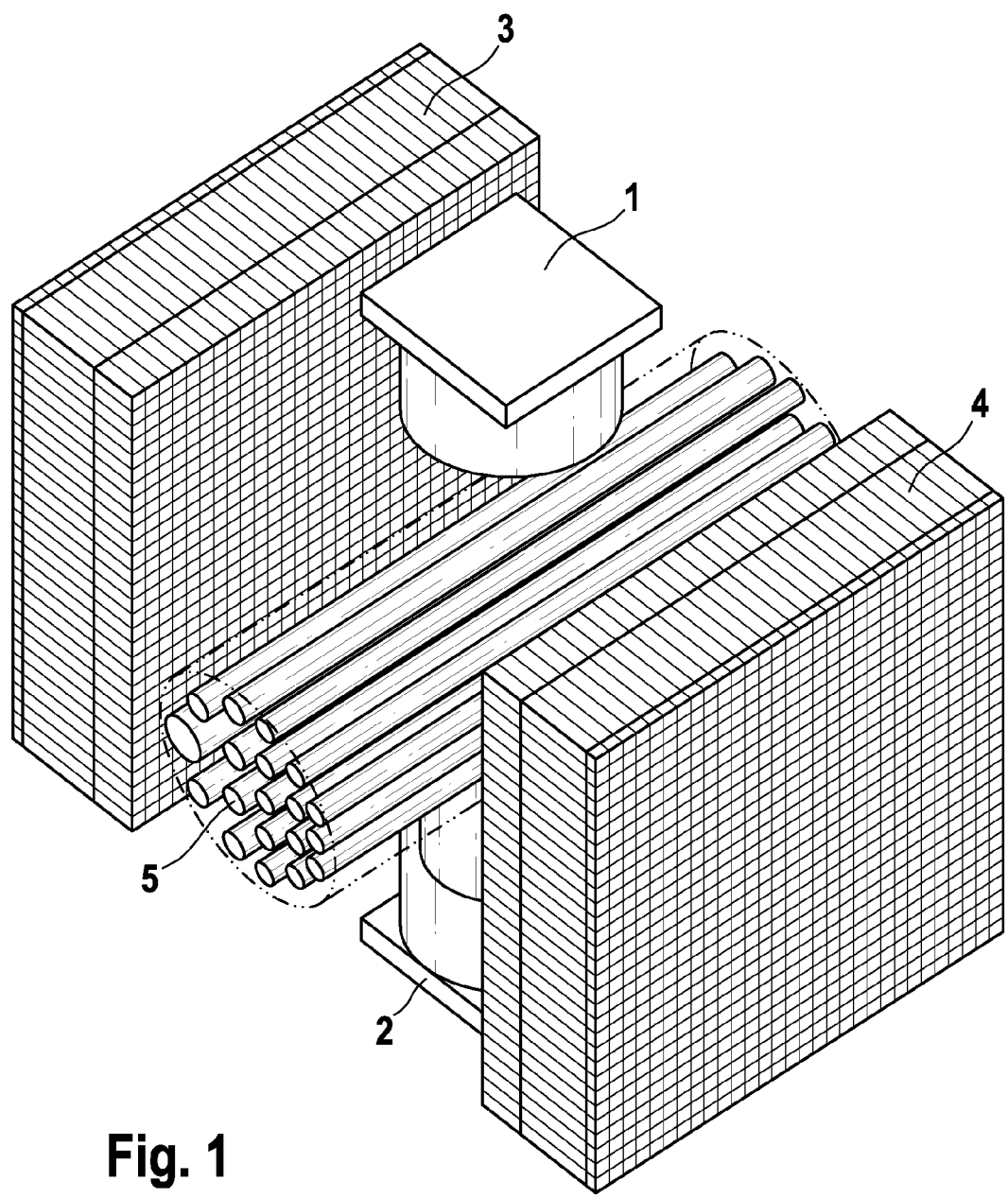
FIG. 1 shows schematically a first preferred embodiment of a dual-modality imaging system according to the invention with two opposed planar gamma-ray detector arrays and two adjacent CCD cameras.

All systems illustrated in FIGS. 1 to 3 are purposely constructed by mounting the PET detector blocks and CCD cameras 8 on a common gantry, that is fully rotational about the imaged objects 5's longitudinal axis, as well as translatable along its longitudinal axis.

Since the optical imaging systems shown in FIGS. 1 to 3 consist of technologically unaltered and in their physical performance unaffected elements (lasers, CCD cameras, filters, . . .) there is no impairment of detection efficiency or spatial resolution as compared to exclusive utilization.

Figure 4:
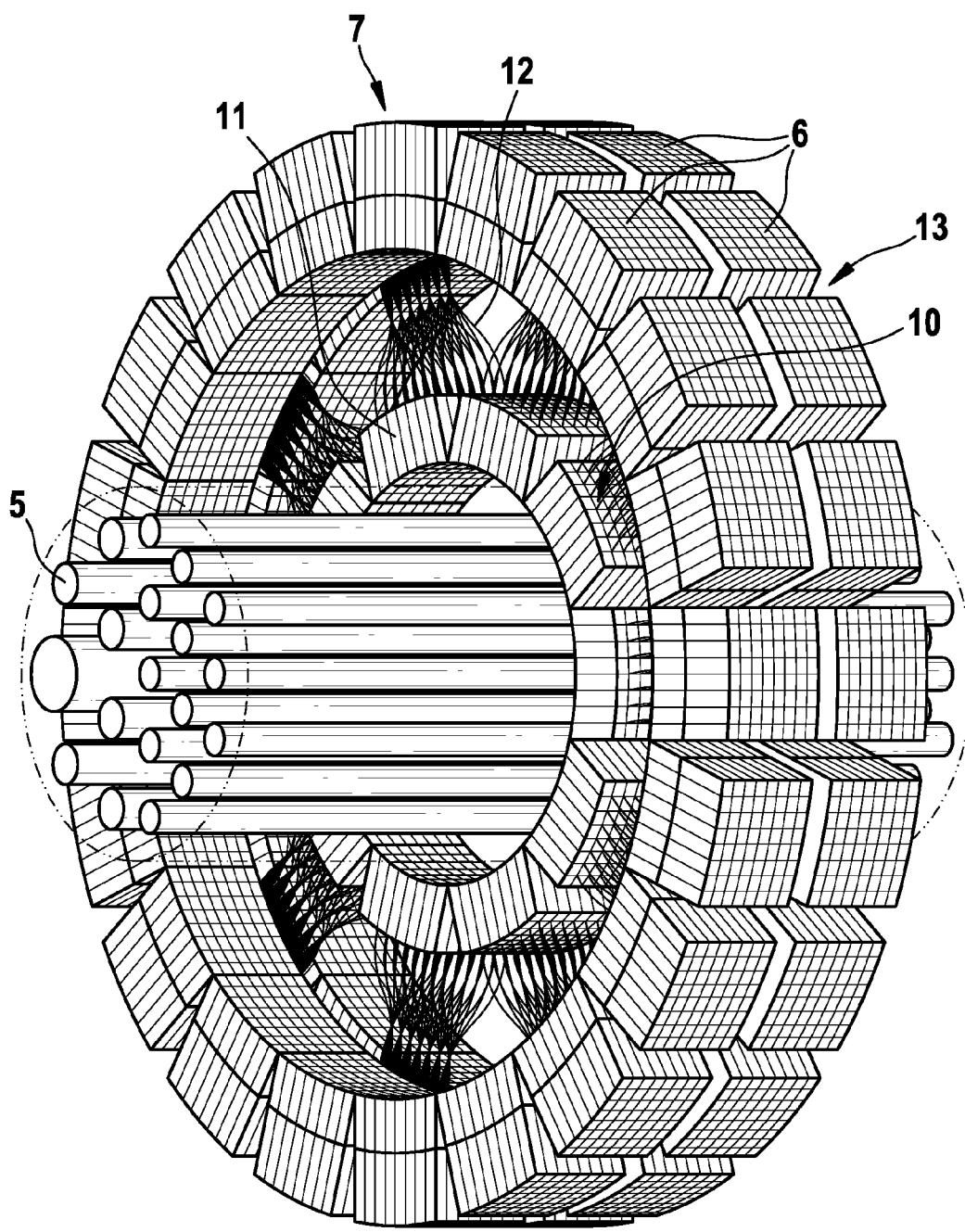
FIG. 4 shows schematically a fourth preferred embodiment of a dual-modality imaging system according to the invention with a ring of gamma-ray detector arrays surrounding a ring of micro-lens arrays.

FIG. 4 shows a fourth preferred embodiment of a dual-modality imaging system according to the present invention.

This dual-modality imaging system comprises a PET scanner with a plurality of gamma-ray detector arrays 6, which are arranged in a ring form 7, surrounding the imaged object 5. The dual-modality imaging system further comprises a plurality of micro-lens arrays 10, each containing a plurality of micro-lenses. The plurality of micro-lens arrays 10 is arranged in a ring structure 11, surrounding the imaged object 5, the ring structure 11 being arranged within the ring form 7 of gamma-ray detector array 6. Therefore, the micro-lens arrays 10 form the system's inner (optical) detector ring. This embodiment of a dual-modality imaging system according to the invention does not employ CCD cameras for detecting projection data. It uses a radial cylindrical lattice of micro-lens arrays, which are mounted in front of the PET detector blocks instead. The PET detector blocks 6 for the detection of high energy (511 keV) isotopic photons are distanced in radial extension to the optical detectors 10. Although the PET detectors 6 can consist of state-of-the-art detection materials (pixelized crystals optically mounted to position-sensitive photo multiplier tubes), they can be custom-manufactured to reflect the block geometry specified for the micro-lens array blocks 10. Even though parts of the optical detection system (micro-lens array 10, optical fibres 12, fibre mounting plates) are within the field-of-view of the PET sub-system, the optical system is insensitive for isotopic photons and the PET system is (nearly) unaffected by the optical parts as the high energy photons penetrate the corporated materials with very small attenuation and scattering. The optical micro-lens system is "stripping away" optical photons while they have no effect on isotopic photons. Optical fibres 12 are attached to the micro-lenses, leading to the outside of the ring form 7 through spaces 13 between the gamma-ray detector arrays 6. The network of optical fibre bundles integrated into the system can be used to guide laser excitation light from an external multi-wavelength laser (not shown) to the imaged object 5 or to guide emitted light from the imaged object 5 to external photo detector arrays for detection (not shown). Individual fibres 12 can be activated selectively, allowing for a variety of laser excitation patterns.

The number of micro-lens arrays 10 per ring structure 11 is defined by the size of the imaged object 5 and the size of the lens array 11. Considering exemplarily the geometry of a small animal (mouse) system, for a transaxial object diameter of 3 cm and a given lens array size of 1 cm×1 cm, the ring consists of ten radially allocated lens arrays. Micro-lens arrays are available commercially and are currently manufactured from 0.5 cm to 1.27 cm in square size. Each lens array consists of a square, rectangular or hexagonal pattern of packed micro-lenses which are each manufactured with a radius in the range of 0.1 mm to 2 mm. The micro-lens arrays 10 and the gamma-ray detector array 6 can also in this embodiment be mounted on a common rotatable and translatable gantry (not shown), which allows for unconstrained arbitrary orbitral positioning of the optical detectors and optical fibre bundles.

The PET sub-systems considered in FIGS. 1 to 4 can be equipped with pixelated arrays of scintillator materials, such as Bismuth germanate (BGO), Lutetium oxyorthosilicate (LSO), Yttrium orthosilicate (YSO), Cerium doped Lutetium (LYSO), Lutetium aluminum perovskite (LuYAP). These are commercially available from a number of companies (Bicron Inc., Washougal, Wash., and others). The crystals are coupled optically via tapered light collectors to arrays of position-sensitive photomultiplier tubes (PSPMTs, Hamamatsu R8520-00-C12, or others). Commercially available read-out electronics can be used (Sparrow Corp., Port Orange, Fla.). Micro-lens arrays are available from SUSS MicroOptics SA, Neuchatel, Switzerland. Optical fibres, lasers and CCD cameras are available from several manufacturers (Roper Scientific, Inc., Duluth, Ga., and others).

Integrated into all systems as shown in FIGS. 1 to 4 are also (not shown) axially moveable optical filters for wave-length separation. In case of non-tomographic optical imaging, the operator will position the laser/CCD blocks at an optical orbital position for light measurements depending on the present optical probe distribution within the object.

For all proposed scanner designs radio-labelled and optical data are collected according to scanning protocols. Each scan protocol can be arranged consistent with animal and study specific requirements.

The FIGS. 1 to 4 show four possible embodiments of the present invention. However, there are numerous specific detector geometries and material arrangements possible, depending on spatial resolution, energy resolution and system sensitivity requirements.

In order to study the performance of the proposed imaging systems, and particularly to assess possible image artifacts, which the PET system might experience attributable to the integrated optical parts, a number of dedicated Monte Carlo simulation studies have been performed. Performing Monte Carlo simulation studies for any of the imaging modalities discussed has become a broadly accepted standard tool for investigating medical physics instrumentation. All suggested scanner designs shown in FIGS. 1 to 4 were physically simulated. There were no or little quantifiable design-specific artifacts or degradations on PET system performance identified, as all alterations made (PET detector block—CCD replacement, transaxial ring—CCD rotation, . . .) can be corrected within the image reconstruction algorithm.

Figure 5:
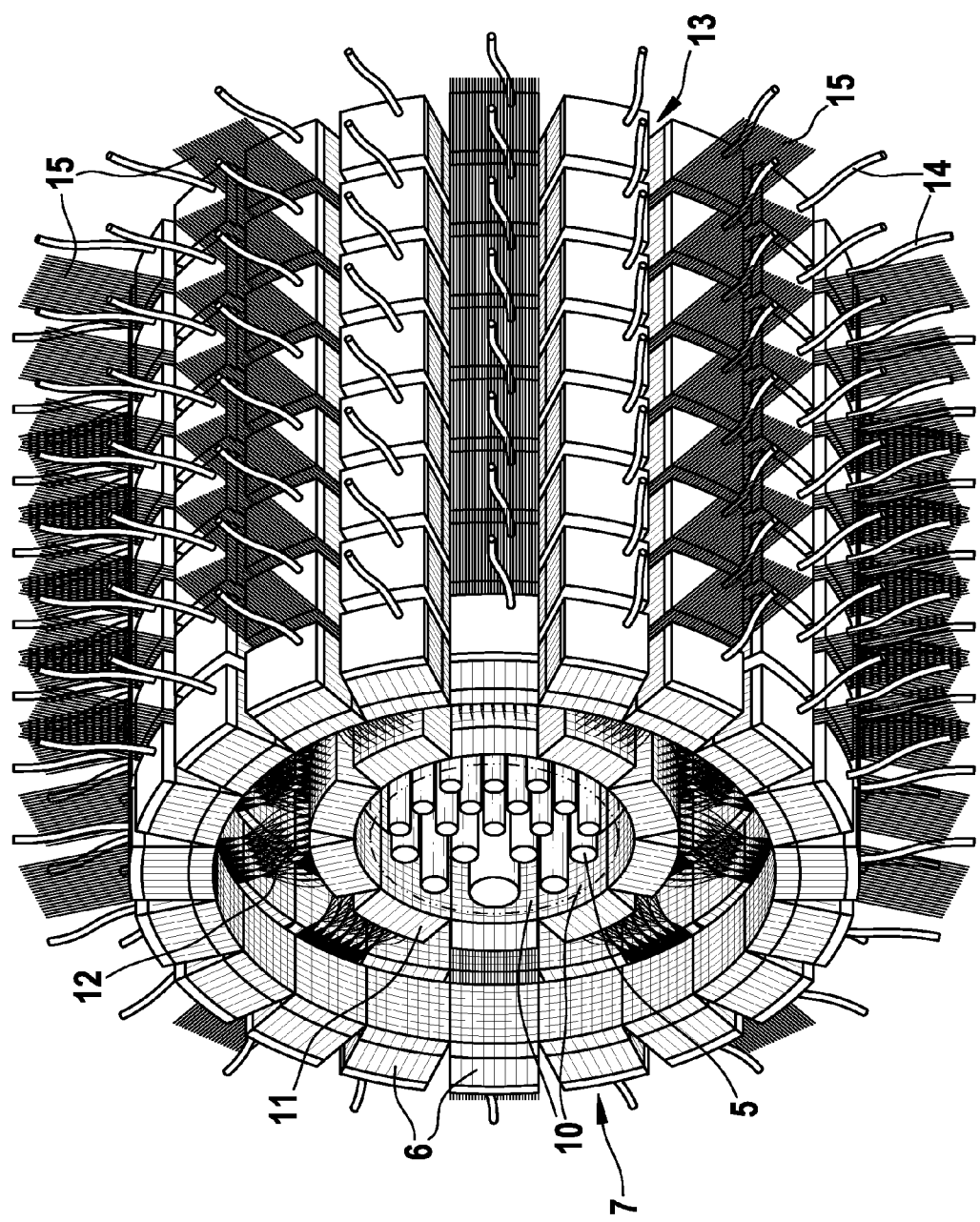
FIG. 5 shows schematically a variation of the fourth embodiment according to FIG. 4 with a larger number of PET detector rings.

FIG. 5 shows a variation of the embodiment as shown in FIG. 4.

The imaged object 5 is along its whole length surrounded by a ring structure 11 of micro-lens arrays 10, which is arranged within a plurality of gamma-ray detector arrays 6 in ring form 7. Six rings of twenty gamma-ray detector arrays 6 each are mounted in a row. Each gamma-ray detector array 6 has an electrical connection 14. The optical fibres 12 which are attached to the micro-lens arrays 10 exit the PET scanner through the spaces 13 between the gamma-ray detector arrays 6 in the form fibre bundles 15. The ring structure 11 is formed by eight rings of ten micro-lens arrays 10 each.

Figure 6:
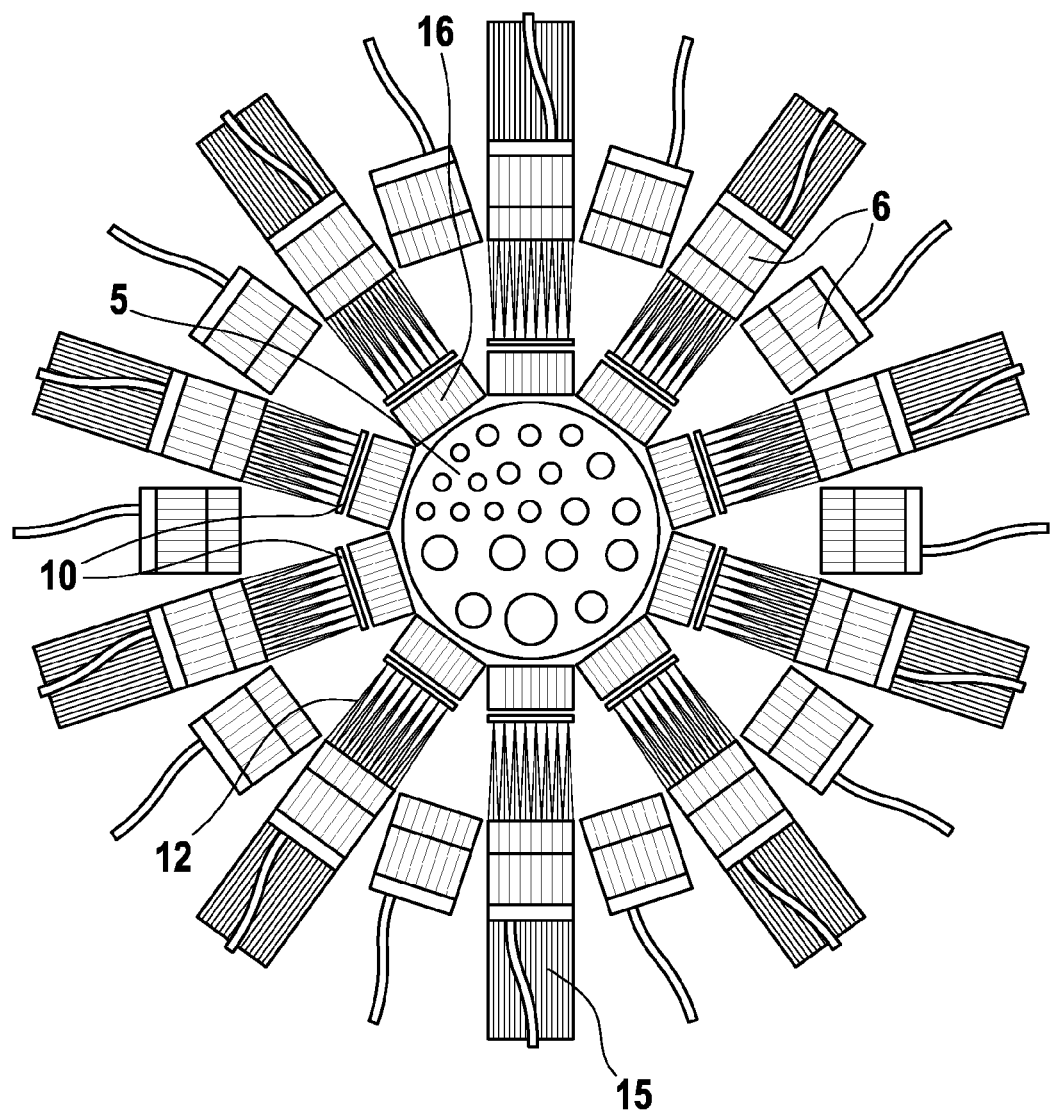
FIG. 6 shows the cross section of the fourth embodiment of FIG. 4.

FIG. 6 shows the cross section of the embodiment as shown in FIG. 4.

In this illustration, the arrangement of all the components of the dual-modality imaging system according to the present invention (micro-lens arrays 10, optical fibres 12, gamma-ray detector arrays 6, fibre bundles 15) around the imaged object 5 can be seen. The system further comprises an optical collimator 16 in front of each micro-lens array 10.

Figure 7:
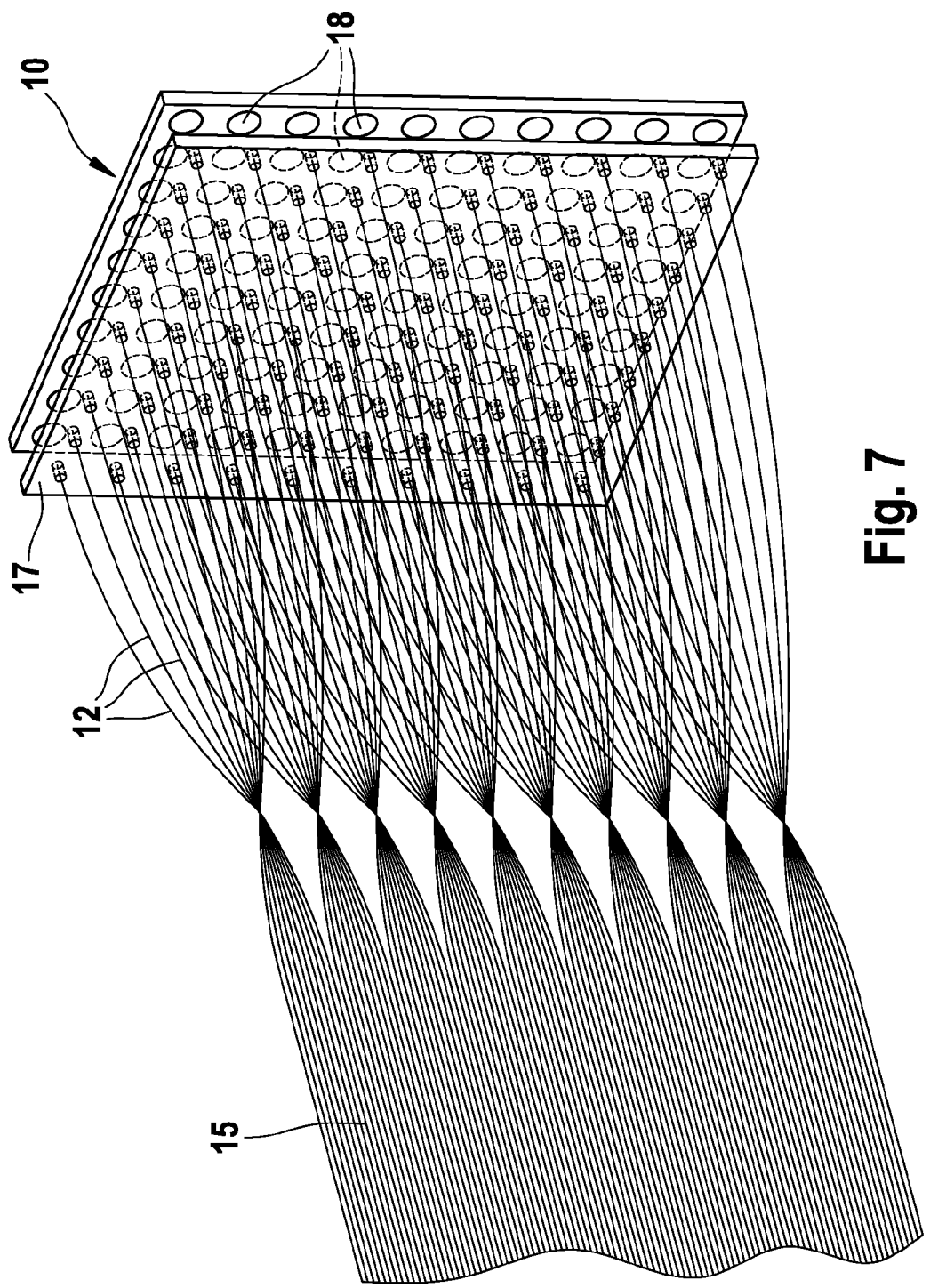
FIG. 7 shows a micro-lens array, which can be used in a dual-modality imaging system according to the invention.

FIG. 7 shows a micro-lens array, which can be used for the present invention.

The micro-lens array 10 (in a square pattern) contains a multi-hole plate 17 and a plurality of mounted micro-lenses 18. A network of optical fibres 12 is mounted on the multi-hole plate 17 such that the focal points of the individual micro-lenses 18 correspond locally to single fibre ending points. The optical fibres merge into a fibre bundle 15.

Figure 8:
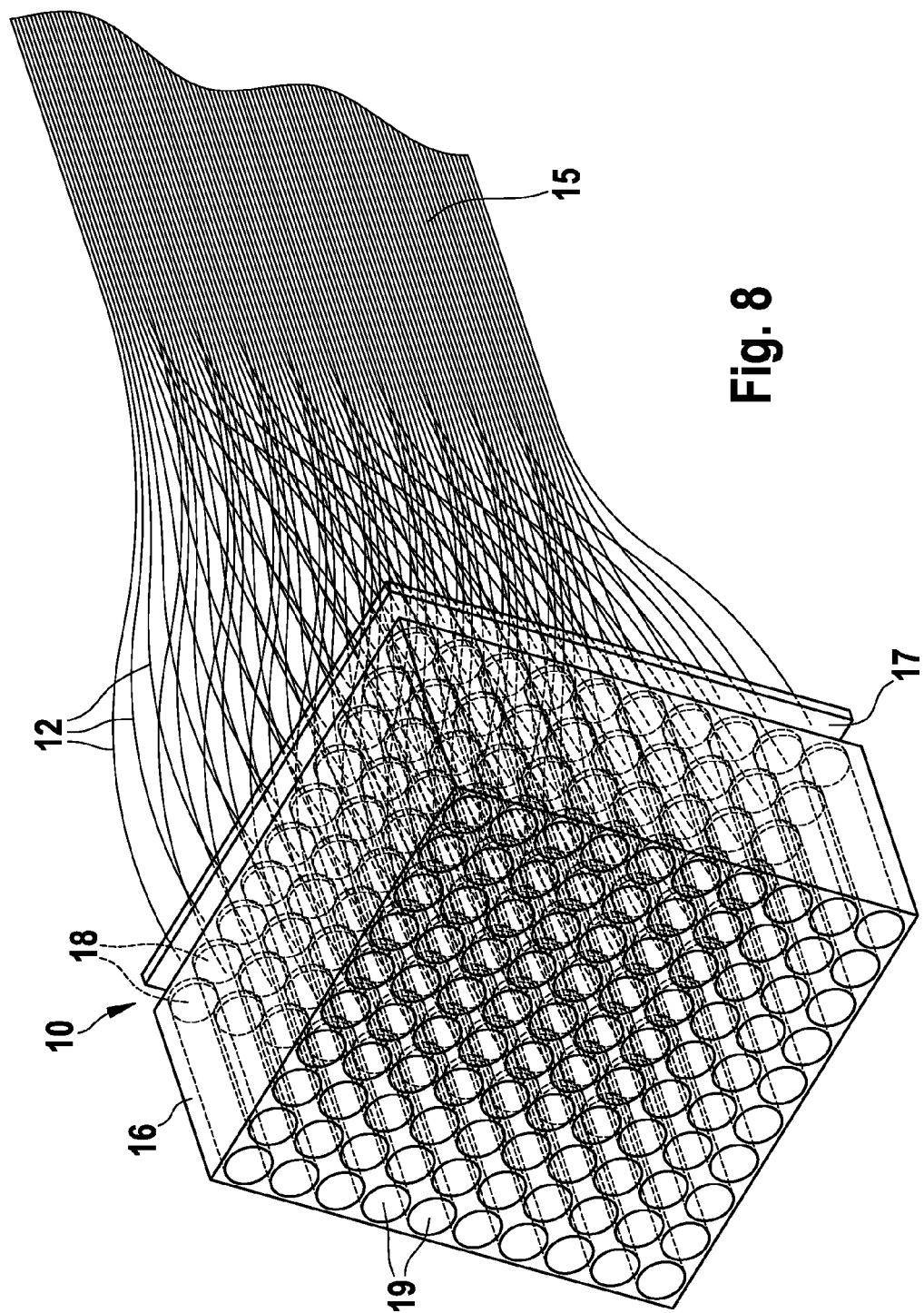
FIG. 8 shows a micro-lens array with an optical collimator, which can be used in a dual-modality imaging system according to the invention.

FIG. 8 shows a micro-lens array with an optical collimator.

In addition to the fibre bundles 15, the optical fibres 12, multi-hole plate 17, and micro-lenses 18, FIG. 8 shows a multi-hole collimator 16, which is mounted in front of the micro-lenses 18, each hole 19 of the collimator 16 corresponding to one micro-lens 18. The purpose of the collimator 16 is to block unwanted light that might produce cross-talk between the fields-of-view of individual micro-lenses 18.

Figure 9:
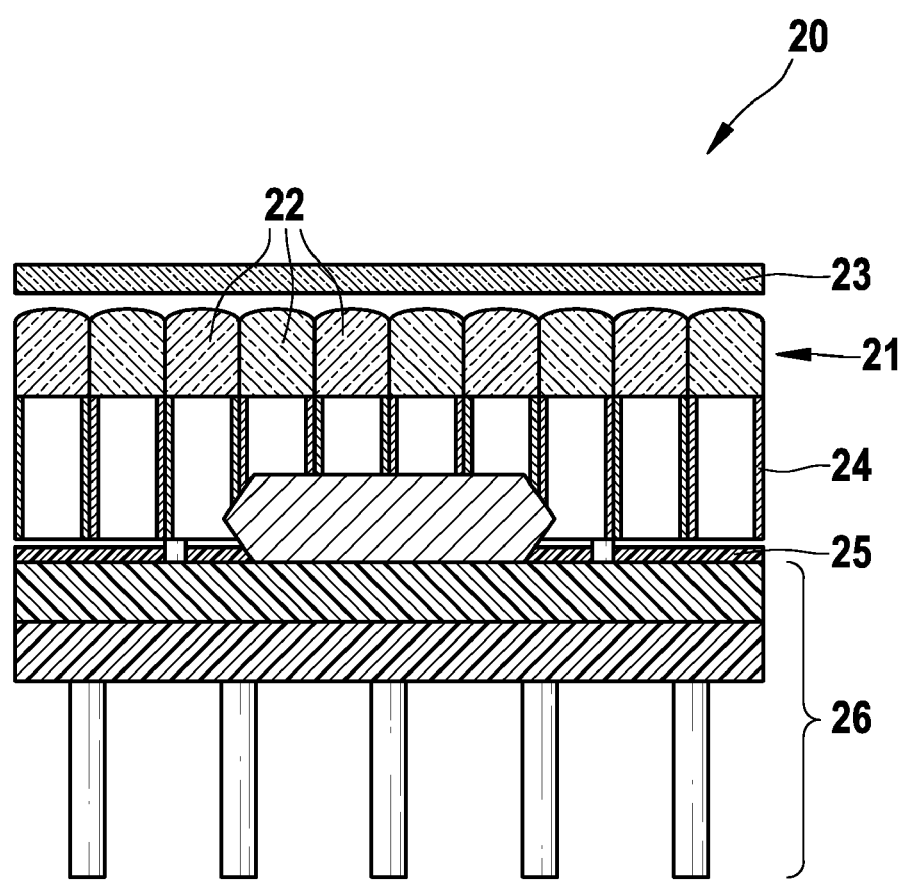
FIG. 9 shows an optical detector block, which can be part of the dual-modality imaging system according to the invention.

FIG. 9 shows an optical imaging detector, which can be part of the dual-modality imaging system according to the invention.

The figure shows a cross-section of a detector block 20. An optical imaging detector of the dual-modality imaging system according to the present invention can comprise one such detector block 20 or a plurality of detector blocks 20. The detector block 20 contains a micro-lens array 21 with a plurality of micro-lenses 22, which are arranged in a two-dimensional lattice. Preferably all micro-lenses 22 have identical geometrical and optical properties, but if necessary for an application, these properties can vary with reference to the individual micro-lenses 22 of the micro-lens array 21. The diameter of the micro-lenses 22 is chosen based upon application-required spatial resolution properties. Exemplarily lens diameters of 0.48 mm and of 1.0 mm have been selected for two different applications.

The detector block 20 further comprises a filter 23 positioned in front of the micro-lens array 21. The filter 23 is that part of the detector block 20, which is closest to the imaged object (not shown). The micro-lens array 21 is mounted behind the filter 23 in radial extension to the imaged object.

The filter 23 is provided e.g. for filtering out laser excitation light when the detector block 20 is used for fluorescence imaging. The filter 23 is not needed for bioluminescence imaging.

On the other side of the micro-lens array 21 an optical collimator 24 is positioned in front of the micro-lens array 21. This photo resist collimator 24 has preferably a hole order and pitch similar to the micro-lens order and pitch of the micro-lens array 21. The collimator 24 is provided to avoid cross-talk between individual fields-of-view of the micro-lenses 22. The thickness of the collimator 24 in radial extension depends upon the space between the back facing surface of the micro-lens array 21 and the virtual focal plane of the micro-lenses 22.

Next to the collimator 24 a large-field photo detector 25 is mounted. The photo detector 25 is positioned at the focal plane of the micro-lens array 21. This photo detector 25 can be a CCD based detector, an APD array, a photo diode array, a CMOS sensor and any other position sensitive light detector. Preferably the photo detector 25 is a CMOS sensor, which shows many advantages in view of its performance (sensitivity, noise characteristics, time resolution, etc.) and in view of its cost. The photo detector 25 transforms the incoming light, which passes the filter 23, the micro-lens array 21 and the optical collimator 24, into an electrical signal.

The micro-lenses 22 of the micro-lens array 21 are distanced by a certain pitch, which should be equal to or a multitude of the photo detector's 25 pitch in order to avoid Moire artefacts in the acquired image. Exemplarily in one experimental setup micro-lenses 22 are used with a lens diameter equal to lens pitch of 0.48 mm. The pitch of an employed CMOS sensor is chosen to be $1/10$ of this (0.048 mm). The photo detector 25 is a position sensitive sensor consisting of a two-dimensional lattice of individual sensor elements.

The overall dimensions of all previously described detector parts 21, 23, 24 and 25 used for image formation and detection should be equal. That is, if the size of a micro-lens array 21 is chosen to delineate a field-of-view of 1 cm×1 cm so should be the sizes of the sensor 25, collimator 24 and filter 23 as well. This is, however, not required for the sole purpose of detection. In principle, detector parts 21, 23 and 24 might be replaceable allowing for modification of imaging characteristics. If additional electronics parts and signal transmission elements 26 are necessary, as in the shown CMOS design, these should be placed outside of the detector's field-of-view (also out of the PET field-of-view).

The detector block 20 of FIG. 9 can either be used for two-dimensional (i.e. planar) or, if assembled or rotated in a certain manner, for fully 3-dimensional tomographic imaging. In most application scenarios a detector block 20 is positioned at a certain distance, but not in contact with the imaged object, with its micro-lens array detector surface oriented orthogonal to the imaged object or portions thereof. The sensitive size of such a detector block 20 can be selected arbitrarily (being constrained by technological processes) but should be governed by the size of the imaged object or portions of it. Exemplarily the detector block size is chosen to be 5 mm (transaxially)×70 mm (axially) such that a whole mouse (in axial extension) can be imaged by view. In another specific application one detector's size is chosen with 25 mm (transaxially)×70 mm (axially). In this case the detector's field-of-view covers an entire mouse.

Figure 10:
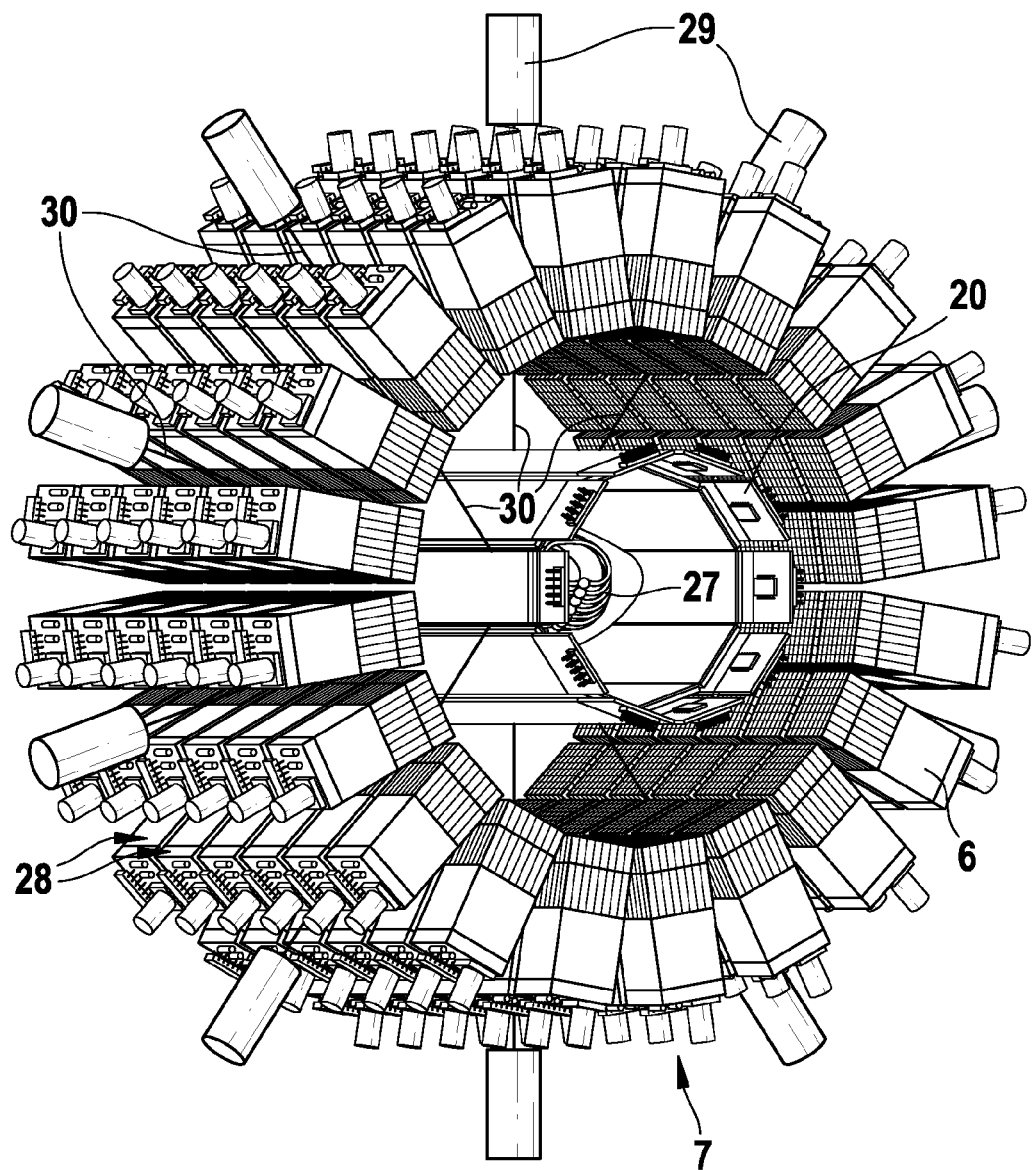
FIG. 10 shows a perspective view of a dual-modality imaging system according to the invention with a plurality of optical detectors comprising position sensitive photo detectors being arranged in a ring structure which is arranged within a ring form of gamma-ray detector arrays.

FIG. 10 shows a perspective view of a dual-modality imaging system according to the invention with a plurality of optical detectors comprising position sensitive photo detectors being arranged in a ring structure which is arranged within a ring form of gamma-ray detector arrays.

Figure 11:
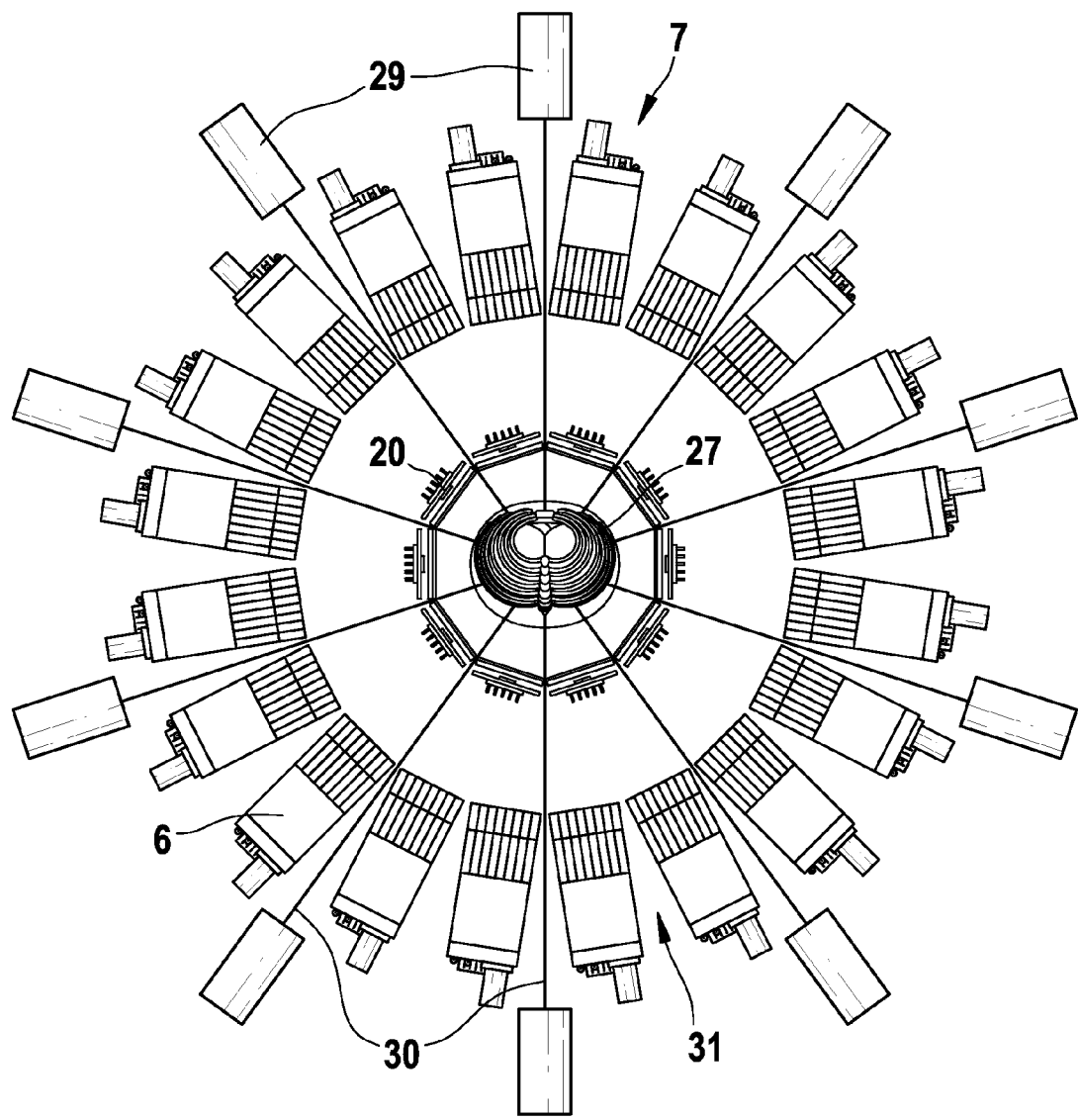
FIG. 11 shows a transaxial view of a dual-modality imaging system according to FIG. 10.

FIG. 11 shows a transaxial view of a dual-modality imaging system according to FIG. 10.

Figure 12:
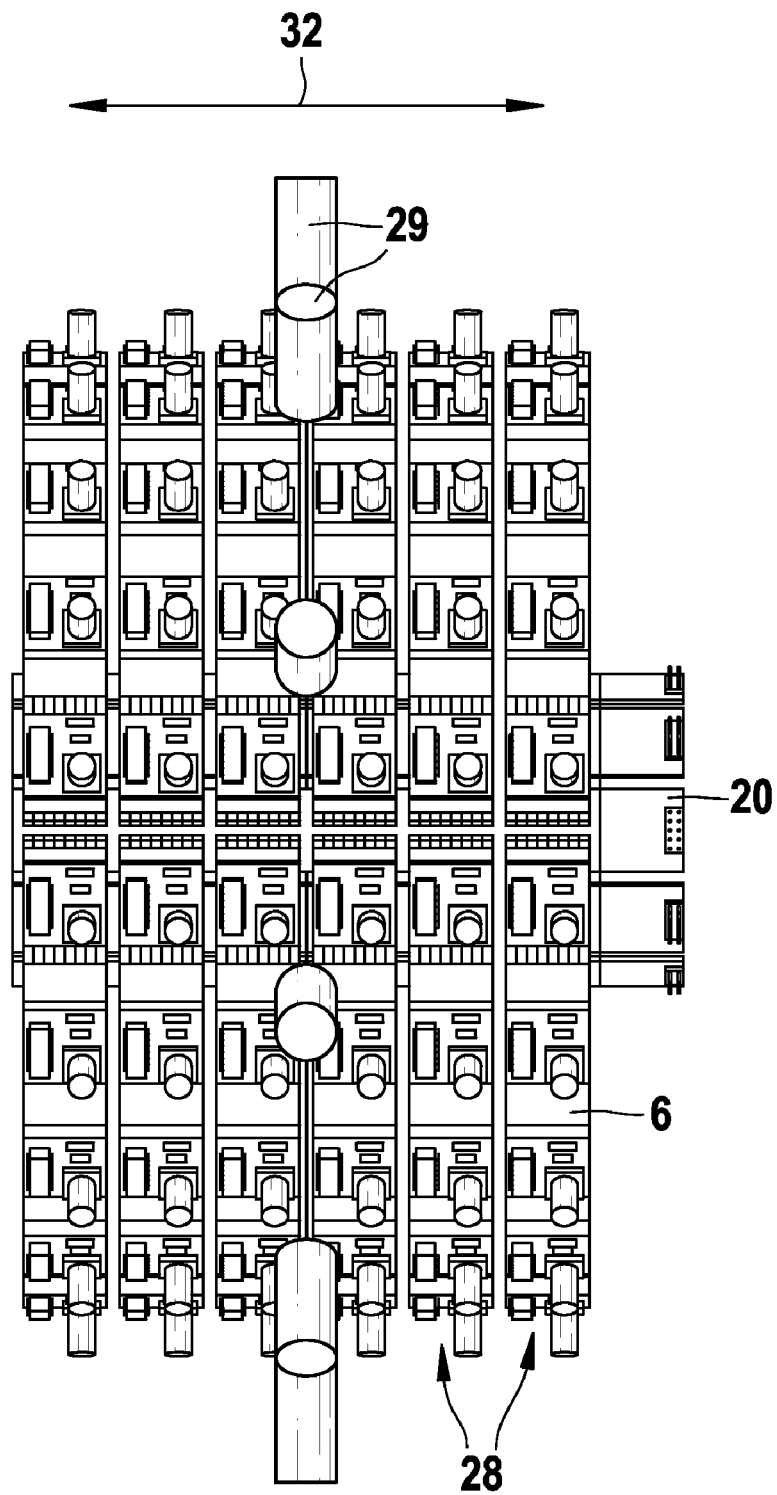
FIG. 12 shows an axial view of a dual-modality imaging system according to FIG. 10.

FIG. 12 shows an axial view of a dual-modality imaging system according to FIG. 10.

In FIGS. 10, 11 and 12 a plurality of optical imaging detector blocks 20 according to FIG. 9 are arranged in a ring structure surrounding an imaged object 27, in this case a mouse phantom. This dual-modality imaging system is constructed by combination of these optical imaging detector blocks 20 with a PET system comprising a plurality of gamma-ray detector arrays 6 arranged in a ring form 7 surrounding the imaged object 27. The gamma-ray detector arrays 6 are capable of detecting high-energy (511 keV) isotopic photons. They are distanced in radial extension to the optical detectors 20, which form an inner cylinder. Both sub-systems are mounted on a common gantry. Even though the optical detection system (comprising detector blocks 20 with filters, micro-lens arrays, photo detectors and light collimators) is located within the field-of-view of the PET-subsystem, the optical system is insensitive for isotopic photons and the PET system is (nearly) unaffected by the optical detector blocks 20, as high energy photons are only minimally affected by attenuation and scattering within the incorporated materials. The optical micro-lens system is "stripping away" optical photons, having no effect on isotopic photons. The sizes of the optical/PET detector blocks can be selected arbitrarily, but should be governed by the size of the imaged object 27 or portions of it. Exemplarily the optical detector size is chosen to be 10 mm (transaxially)×70 mm (axially) for all ten cylindrically assembled detector blocks 20 (cylinder diameter equals 32 mm) such that a whole mouse (in axial extension) can be imaged in a single procedure. The micro-lens diameter can be chosen to be 0.480 mm for example. In the PET system as illustrated in FIGS. 10, 11 and 12 there are twenty gamma-ray detector arrays 6 cylindrically allocated per ring 28 with a ring diameter of 70 mm. Each gamma-ray detector array 6 has a sensitive area of 10 mm×10 mm. There are six rings 28 attached to each other. Lasers 29 are positioned at radial extension behind the PET rings 28. They are used for probe excitation in fluorescence imaging. The optical detector arrangement and the PET detectors are arranged in such a way, that laser light beams 30 can be sent through gaps 31 of the individual blocks. Each laser 29 is preferably translatable in a translation direction 32 along its axis of rotation, the entire system (optical detectors 20, PET detectors 6 and lasers 29) being rotatable. This allows for arbitrary probe excitation and improved spatial sampling, particularly of the optical system.

LIST OF REFERENCE NUMBERS

1 First CCD camera
2 Second CCD camera
3 First planar gamma-ray detector array
4 Second planar gamma-ray detector array
5 Imaged object (shown as "Derenzo" phantom)
6 Gamma-ray detector array
7 Ring form
8 CCD camera
9 Vertical axis
10 Micro-lens arrays
11 Ring structure
12 Optical fibres
13 Spaces
14 Electrical connection
15 Fibre bundles
16 Optical collimator
17 Multi-hole plate
18 Micro-lenses
19 Hole
20 Detector block
21 Micro-lens array
22 Micro-lenses
23 Filter
24 Optical collimator
25 Photo detector
26 Electronics parts and signal transmission elements
27 Imaged object
28 Ring
29 Lasers
30 Laser light beams
31 Gaps
32 Translation direction

The invention claimed is:

1. A dual-modality imaging system, wherein a positron emission tomography (PET) scanner for acquiring PET imaging data and at least one optical imaging detector for acquiring optical imaging data are arranged to acquire the PET imaging data and the optical imaging data of an imaged object simultaneously, wherein the at least one optical imaging detector is a non-contact optical imaging detector, said optical imaging detector comprising at least one micro-lens array with a plurality of micro-lenses.

2. The dual-modality imaging system according to claim 1, wherein the at least one optical imaging detector and the PET scanner are mounted on a rotatable gantry.

3. The dual-modality imaging system according to claim 1, wherein the PET scanner comprises at least two gamma-ray detector arrays.

4. The dual-modality imaging system according to claim 3 wherein the gamma-ray detector arrays and the at least one optical imaging detector are radially relocatable.

5. The dual-modality imaging system according to claim 1, wherein the PET scanner comprises two opposed planar gamma-ray detector arrays.

6. The dual-modality imaging system according to claim 5, wherein the at least one optical imaging detector is arranged adjacent to the planar gamma-ray detector arrays in a plane which is perpendicular to the planar gamma-ray detector arrays.

7. The dual-modality imaging system according to claim 5, wherein the PET scanner comprises a plurality of planar or curved gamma-ray detector arrays, which are arranged in a ring form.

8. The dual-modality imaging system according to claim 7, wherein two of the gamma-ray detector arrays at a time are diametrically opposed.

9. The dual-modality imaging system according to claim 7, wherein the at least one optical imaging detector is integrated into the ring form.

10. The dual-modality imaging system according to claim 7, wherein the ring form is tilted about a first angle in one direction and the at least one optical imaging detector is tilted about a second angle in an opposite direction with respect to the imaged object.

11. The dual-modality imaging system according to claim 10, wherein the first angle is in the range from 5 to 25 degrees and the second angle is in the range from 5 to 25 degrees.

12. The dual-modality imaging system according to claim 1, comprising two opposed optical imaging detectors.

13. The dual-modality imaging system according to claim 1, wherein the optical imaging detector comprises a CCD camera and/or at least one position sensitive photo detector.

14. The dual-modality imaging system according to claim 13, wherein the position sensitive photo detector is at least one sensor selected from the group of CCD based detector, APD array, photo diode array or CMOS sensor.

15. The dual-modality imaging system according to claim 1, wherein at least one position sensitive photo detector is positioned at a focal plane of one of the micro-lens arrays.

16. The dual-modality imaging system according to claim 1, wherein each micro-lens is connected to an optical fibre.

17. The dual-modality imaging system according to claim 16, wherein each micro-lens is connected to a photo detector or to a light source via the optical fibre.

18. The dual-modality imaging system according to claim 1, wherein the at least one micro-lens array has a square, rectangular or hexagonal pattern.

19. The dual-modality imaging system according to claim 1, wherein a plurality of planar or curved micro-lens arrays or a plurality of optical detectors comprising position sensitive photo detectors is arranged in a ring structure.

20. The dual-modality imaging system according to claim 19, wherein the ring structure is arranged within a ring form of gamma-ray detector arrays.

21. The dual-modality imaging system according to claim 1, wherein each micro-lens has a diameter in a range from 0.1 to 2 mm.

22. The dual-modality imaging system according to claim 1, wherein an optical collimator is positioned in front of each micro-lens array.

23. A method for dual-modality imaging of an imaged object, wherein PET imaging data and optical imaging data of the imaged object are acquired simultaneously by a PET scanner and at least one non-contact optical imaging detector.

24. The method of claim 23, including the steps of reconstructing a PET image and an optical image by the acquired PET and optical imaging data and displaying at least one of the PET image, the optical image or a fused PET/optical image on a display device.

25. The dual-modality imaging system according to any one of claims 1 and 2 wherein the at least one optical imaging detector is radially relocatable.

* * * * *